United States Patent
Faour (10) Patent No.: US 6,599,284 B2
(45) Date of Patent: Jul. 29, 2003

(54) OSMOTIC DEVICE HAVING A PREFORMED PASSAGEWAY THAT INCREASES IN SIZE

(75) Inventor: Joaquina Faour, Buenos Aires (AR)

(73) Assignee: Osmotica Corp., Tortola (VG)

(*) Notice: Subject to any disclaimer, the term of this patent is extended or adjusted under 35 U.S.C. 154(b) by 81 days.

(21) Appl. No.: 09/728,859

(22) Filed: Nov. 30, 2000

(65) Prior Publication Data

US 2002/0099361 A1 Jul. 25, 2002

Related U.S. Application Data (60) Provisional application No. 60/177,427, filed on Jan. 21, 2000.

(51) Int. Cl.⁷ .................................................. A61K 9/22
(52) U.S. Cl. ................................. 604/892.1; 604/890.1
(58) Field of Search ............................. 604/890, 892.1, 604/897

(56) References Cited

U.S. PATENT DOCUMENTS

| | | | | |
|---|---|---|---|---|
| 3,916,899 A | * | 11/1975 | Theeuwes et al. ........... 128/260 |
| 4,285,987 A | * | 8/1981 | Ayer et al. ....................... 427/3 |
| 4,449,983 A | * | 5/1984 | Cortese et al. ............... 604/892 |
| 4,455,143 A | * | 6/1984 | Theeuwes et al. ........... 604/890 |
| 4,615,698 A | * | 10/1986 | Guittard et al. ............. 604/892 |
| 4,627,851 A | * | 12/1986 | Wong et al. ................. 604/892 |
| 4,685,918 A | * | 8/1987 | Amidon et al. ............. 604/892 |
| 4,693,886 A | * | 9/1987 | Ayer ............................. 424/15 |
| 4,743,248 A | * | 5/1988 | Bartoo et al. ............. 604/892.1 |
| 4,765,989 A | * | 8/1988 | Wong et al. ................. 424/473 |
| 4,857,330 A | * | 8/1989 | Stephens et al. ............ 424/424 |
| 4,960,416 A | * | 10/1990 | Stephens et al. ......... 604/892.1 |
| 5,028,664 A | * | 7/1991 | Ohmura et al. ............. 525/217 |
| 5,057,321 A | * | 10/1991 | Edgren et al. .............. 424/413 |
| 5,082,668 A | * | 1/1992 | Wong et al. ................. 424/473 |
| 5,108,756 A | * | 4/1992 | Curatolo ...................... 424/450 |
| 5,221,536 A | * | 6/1993 | Edgren et al. .............. 424/473 |
| 5,240,713 A | | 8/1993 | Ayer |
| 5,266,332 A | * | 11/1993 | Dong et al. ................. 424/473 |
| 5,273,752 A | | 12/1993 | Ayer et al. |
| 5,413,572 A | * | 5/1995 | Wong et al. ............. 604/892.1 |
| 5,650,170 A | * | 7/1997 | Wright et al. ............... 424/473 |
| 5,718,700 A | * | 2/1998 | Edgren et al. ........... 604/892.1 |
| 5,824,341 A | * | 10/1998 | Seth et al. .................. 424/473 |
| 5,842,476 A | * | 12/1998 | Wright et al. ............... 128/898 |
| 5,869,096 A | * | 2/1999 | Barclay et al. ............. 424/468 |
| 5,897,878 A | * | 4/1999 | Dong et al. ................. 424/473 |
| 5,914,131 A | * | 6/1999 | Merrill et al. .............. 424/473 |
| 6,004,582 A | * | 12/1999 | Faour et al. ................. 424/473 |
| 6,419,952 B2 | * | 7/2002 | Wong et al. ................. 424/463 |
| 6,514,530 B2 | * | 2/2003 | Skluzacek et al. ......... 424/468 |

* cited by examiner

Primary Examiner—Henry Bennett
Assistant Examiner—Nihir Patel
(74) Attorney, Agent, or Firm—Rick Matos; Innovar, L.L.C.

(57) ABSTRACT

The present invention provides a simple and improved osmotic device (1) that is capable of providing a controlled release of active agent contained in the core (4) through a preformed passageway (5) into an environment of use. The preformed passageway (5) increases in size during use of the osmotic device (1) thereby increasing the release rate of the active agent, enabling the release of large particles containing active agent, and enabling the release of active agents that are substantially insoluble in the environment of use.

62 Claims, 3 Drawing Sheets

OSMOTIC DEVICE HAVING A PREFORMED PASSAGEWAY THAT INCREASES IN SIZE

CROSS-REFERENCE TO RELATED APPLICATIONS

The present application claims the priority of U.S. provisional application for patent Ser. No. 60/177,427 filed Jan. 21, 2000.

FIELD OF THE INVENTION

This invention pertains to an osmotic device for the controlled delivery of a maximum amount of active agents to an environment of use. More particularly, it pertains to an osmotic device that increases in size during use thereby providing a relatively faster and more complete delivery of active agent.

BACKGROUND OF THE INVENTION

Osmotic devices have demonstrated utility in delivering useful active agents such as medicines, nutrients, food products, pesticides, herbicides, germicides, algaecides, chemical reagents, and others known to those of ordinary skill to an environment of use in a controlled manner over prolonged periods of time. Known devices include tablets, pastilles, pills or capsules and others that use osmotic pressure to control the release of the active agent contained in the core of the osmotic device. Some osmotic devices may also include layers comprising one or more materials that are subject to erosion or that slowly dissolve in the environment of use thereby gradually dispensing the active agent. Known devices generally suffer from an inability to dispense all or substantially all the active agent from the core prior to the loss of osmotic pressure that occurs at osmotic equilibrium.

U.S. Pat. No. 4,088,864 to Theeuwes et al. ("Theeuwes et al. '864) discloses a high speed process for forming outlet passageways in the walls of osmotic devices for release of the contents of the osmotic device comprising: a) moving the pills in succession along a predetermined path at a predetermined velocity; b) tracking the moving pills seriatim at said velocity with a laser of a wavelength which is absorbable by said walls by oscillating the optical path of the laser back and forth over a predetermined section of the pill path at said velocity; c) firing the laser during said tracking; d) adjusting the laser beam dimension at said wall, the laser power and the firing duration such that the laser beam is capable of piercing the wall; and e) forming, with the laser beam, an outlet passageway 4 to 2000 microns in diameter in the wall. Theeuwes et al. '864 does not disclose a process for forming a passageway that increases in size during use of the osmotic device.

Theeuwes et al. '864 also discloses an apparatus for forming outlet passageways in the walls of osmotic devices for release of the contents of the osmotic device comprising: a) a support frame; b) a laser operating in a pulse mode; c) an optical pill tracking mechanism; d) a rotary pill indexer; and e) an electrical power supply to supply and control power for the laser, the tracking mechanism, and the indexer. Theeuwes et al. '864 does not disclose an apparatus for forming a preformed passageway that increases in size during use of the osmotic device.

U.S. Pat. No. 4,014,334 to Theeuwes et al. ("Theeuwes et al. '334") discloses an osmotic device for the controlled and continuous delivery of a drug wherein the device comprises: a) a core containing a drug and an osmotic agent; b) a semipermeable laminate, surrounding the core, which includes an external semipermeable lamina and an internal semipermeable lamina; and c) a passageway which communicates the core with the exterior of the device. The two semipermeable laminae maintain their chemical and physical integrity in the presence of the drug and fluid from the environment. The passageway of Theeuwes et al. '334 includes a passageway, orifice or bore through the laminate formed by mechanical procedures, or by eroding an erodible element, such as a gelatin plug, in the environment of use. Theeuwes et al. '334 does not disclose a preformed passageway that increases in size during use of the osmotic device.

U.S. Pat. No. 4,576,604 to Guittard et al. ("Guittard et al. '604") corresponds to Argentina Patent No. 234,493 and discloses several different embodiments of an osmotic device having a drug in the core and at least one lamina surrounding the core. Specifically, one embodiment of the osmotic device comprises: a) a core containing a drug formulation which can include an osmotic agent for controlled release of the drug; b) a semipermeable wall comprising an inner semipermeable lamina, a middle microporous lamina, and an outer water soluble lamina containing drug; and c) a passageway which communicates the core with the exterior of the device. Guittard et al. '604 does not disclose a preformed passageway that increases in size during use of the osmotic device.

U.S. Pat. No. 4,673,405 to Guittard et al ("Guittard et al. '405") discloses an osmotic device comprising: a) a core, or compartment, containing a beneficial agent; b) an inert semipermeable wall containing a beneficial agent surrounding the core; and c) at least one passageway in the wall of the osmotic device which is formed when the osmotic device is in the fluid environment of use and the fluid contacts and thus releases the beneficial agent in the wall, wherein the formed passageway communicates with the compartment in the osmotic device and the exterior of the device for dispersing the beneficial agent from the compartment when the device is in the fluid environment of use. Guittard et al. '405 discloses the use of an erodible element to form the passageway; however, it does not disclose a preformed passageway that increases in size during use of the osmotic device.

U.S. Pat. No. 5,558,879 to Chen et al. ("Chen et al. '879") discloses a controlled release tablet for water soluble drugs in which a passageway is formed in the environment of use, i.e., the GI tract of a person receiving the formulation. Specifically, the controlled release tablet consists essentially of: a) a core containing a drug, 5–20% by weight of a water soluble osmotic agent, a water soluble polymer binder and a pharmaceutical carrier; and b) a dual layer membrane coating around the core consisting essentially of: (1) an inner sustained release coating containing a plasticized water insoluble polymer and a water soluble polymer; and (2) an outer immediate release coating containing a drug and a water soluble polymer. Although Chen et al '879 discloses the formation of a passageway in a controlled release tablet in an environment of use to form an osmotic tablet, the passageway is not a preformed passageway that increases in size during use of the osmotic device.

U.S. Pat. No. 4,810,502 to Ayer et al. ("Ayer et al. '502") discloses an osmotic dosage form for delivering pseudoephedrine (Ps) and brompheniramine (Br) which comprises: a) a core containing Ps and Br; b) a wall surrounding the core comprising cellulose acylate and hydroxypropylcellulose; c) a passageway in the wall for delivering the drug; and d) a lamina on the outside of the wall comprising Ps, Br, at least one of hydroxypropylcellulose and hydroxypropyl methylcellulose, and poly(ethylene oxide) for enhancing the mechanical integrity and pharmacokinetics of the wall. Ayer et al. '502 does not disclose a preformed passageway that increases in size during use of the osmotic device.

U.S. Pat. No. 4,801,461 to Hamel et al. ("Hamel et al '461") discloses an osmotic dosage form for delivering pseudoephedrine (Ps). Specifically, the osmotic dosage form comprises: a) a core containing varying amounts of Ps; b) a semipermeable wall surrounding the core comprising varying amounts of cellulose acetate or cellulose triacetate and varying amounts of hydroxypropylcellulose; c) a passageway in the wall for delivering the drug from the core; and optionally d) a lamina on the outside of the wall comprising Ps. The core can also contain one or more of sodium chloride, microcrystalline cellulose, hydroxypropyl methylcellulose, magnesium stearate, and poly(vinylpyrrolidone). The passageway of this device can extend through the semipermeable wall alone or through both the semipermeable wall and the outer lamina. The passageway also includes materials that erode or leach in the environment of use. A variety of erodible materials are listed as suitable for use in forming the passageway. Hamel et al. '461 does not, however, disclose a preformed passageway that increases in size during use of the osmotic device.

U.S. Pat. No. 5,681,584 to Savastano et al. ("Savastano et al. '584") discloses a controlled release drug delivery device comprising: a) a core containing a drug, an optional osmotic agent and optional excipients; b) a delayed release jacket comprising at least one of a binder, an osmotic agent and a lubricant surrounding the core; c) a semipermeable membrane surrounding the delayed release jacket and optionally having a passageway; d) a drug-containing layer either on the outside of the semipermeable membrane or between the semipermeable membrane and the delayed release jacket; and e) an optional enteric coat either on the outside of the drug-containing layer, between the drug-containing layer and the semipermeable membrane or on the outside of the semipermeable membrane when the drug-containing layer is between the delayed release jacket and the semipermeable membrane. Thus, the device of Savastano et al. '584 does not provide for release of active agent via a preformed passageway that increases in size during use of the osmotic device.

U.S. Pat. No. 6,004,582 to Faour et al. (Faour et al. '582) discloses a multi-layered osmotic device comprising a core surrounded by a semipermeable membrane having a preformed hole in it. The hole is subsequently plugged by an inert erodible water soluble coating and then covered with a water soluble drug-containing coating. This patent does not disclose an osmotic device having a preformed passageway that increase in size during use.

U.S. Pat. No. 5,873,793 to Emerton et al. (Emerton et al. '793) and U.S. Pat. No. 5,376,771 to Roy (Roy '771) disclose laser apparatuses capable of simultaneously forming a plurality of holes on the semipermeable membrane of an osmotic device. These patents do not disclose an osmotic device having a preformed passageway that increase in size during use.

Additional exemplary osmotic devices for the controlled delivery of active agents are described in U.S. Pat. No. 3,845,770 and Argentina Patent No. 199,301 which disclose an osmotic device formed by a wall that surrounds a compartment-housing agent. The wall has a passageway or orifice that links the compartment to the environment of use. The wall is made of semipermeable material that is semipermeable to an external fluid and impermeable to an active agent within the device. Neither of these patents discloses a preformed passageway that increases in size during use of the osmotic device.

While the prior art discloses a wide variety of release mechanisms used in osmotic devices, no single release mechanism provides a passageway designed to increase in size during use so that controlled delivery of all or substantially all the amount of active agent is provided or so that the rate of release of the drug increases over time. A method of making such an osmotic device has now been discovered. The present osmotic device overcomes many of the disadvantages inherent in related prior art osmotic devices because it is capable of providing approximately complete delivery of the active substance contained in the core and an increased release rate of active substance during use, and it enables release of large particle size and/or generally insoluble active agents.

SUMMARY OF THE INVENTION

Almost invariably for prior art devices, not all active agent is released before osmotic equilibrium is reached. The present invention, however, overcomes this disadvantage by providing an osmotic device having a preformed passageway that increases in size during use, thereby allowing controlled delivery to an environment of use of an active substance contained in the core of the osmotic device. The present invention also provides a method for making an osmotic device having a preformed passageway that increases in size during use. The benefits provided by the present invention include: 1) approximately complete delivery of the active substance contained in the core; 2) an increased release rate of active substance during use as the increase in size of the passageway permits more of the contents of the core to be released more quickly through the larger passageway; and 3) enablement of the release of large particle size and/or generally insoluble active agents.

One aspect of the present invention provides an osmotic device for the controlled delivery of approximately all of an active substance contained in the core of the osmotic device, wherein the osmotic device comprises: a) a core comprising an active agent, such as nifedipine, at least one osmopolymer, and at least one excipient; b) a semipermeable membrane surrounding the core; c) a preformed passageway in the semipermeable membrane for release of the contents of the core where the passageway increases in size during use of the osmotic device; wherein the passageway provides an increased release rate of active agent during use as compared to an osmotic device not having such a passageway; and the passageway permits release of approximately all of the contents of the core.

Specific embodiments of the invention include those embodiments wherein: a) at least 80% of the active agent is released by the end of use; b) at least 90% of the active agent is released by the end of use; c) the preformed passageway increases in size from its initial size by at least 10%; d) the preformed passageway increases in size from its initial size by at least 25%; e) the preformed passageway increases in size from its initial size by at least 50%; f) the preformed passageway increases in size from its initial size by at least 75%; g) the preformed passageway increases in size from its initial size by at least 100%; h) the preformed passageway increases in size because of mechanical means used during manufacture; i) the preformed passageway expands in size by dissolution or breakage of the semipermeable membrane; j) the preformed passageway expands in size in a predetermined manner; k) the core contains a swellable material; l) the core comprises a nucleus that is coated with active agent and at least one excipient; m) the exterior of the semipermeable membrane has at least one coating that effects the operation of the osmotic device in a manner according to the properties of the coating; and/or n) the preformed passageway increases in size due to an increase in the viscosity, molecular weight, or degree of substitution of the at least one excipient in the core.

One aspect of the present invention provides a method of preparing the osmotic device, wherein a core comprising an active agent and at least one excipient is covered with a semipermeable membrane that is perforated to form at least one preformed passageway that increases in size during use of the osmotic device. In this aspect, the invention provides a method of preparing an osmotic device having a preformed passageway that increases in size during use, wherein the method comprises the steps of: a) forming a core comprising an active agent, such as nifedipine; b) covering the core with a semipermeable membrane; c) perforating the semipermeable membrane with a laser to form a preformed passageway, wherein the laser generally delivers a laser beam of sequential pulses having a predetermined pulse period of greater duration than a pulse period used to make similar osmotic devices that do not have passageways that increase in size; and the laser beam is generally adjusted to fire with a predetermined pulse width of lesser duration than a pulse width used to make similar osmotic devices that do not have passageways that increase in size.

Other aspects of the invention provide a method of making the osmotic device wherein the preformed passageway is formed by other mechanical means; by variations in the viscosity, the molecular weight, or the degree of substitution of the at least one excipient; by the use of plasticizers in the semipermeable membrane; or by the use of a brittling agent.

The present invention further provides a method for using the osmotic device having a passageway that increases in size during use, wherein the osmotic device is generally used in a manner to provide a therapeutic effect on a human.

The at least one excipient is independently selected at each occurrence from the group consisting of an osmagent, an osmopolymer, a lubricant, a glidant, adsorbent, antioxidant, buffering agent, colorant, flavorant, sweetening agent, tablet antiadherent, binder, tablet and capsule diluent, tablet direct compression excipient, tablet disintegrant, tablet or capsule opaquant and/or tablet polishing agent.

The preformed passageway increases in size in a predetermined manner or in a random manner, depending on the method used to form the passageway. The size of the preformed passageway increases from its initial size over time, up to a size as determined by the method and materials used to form the osmotic device. The passageway does not generally decrease in size after all or approximately all of the contents of the core have been released.

The active agents can include compounds such as biologically or pharmacologically active agents, medicines, nutrients, food products, insecticides, pesticides, herbicides, germicides, algaecides, fungicides, chemical reagents, growth regulating substances, parasiticides, sex steriliants, fertility promoters, biocides, rodenticides, disinfectants, anti-oxidants, plant growth promoters, preservatives, fermentation agents, fertility inhibitors, air purifiers, microorganism attenuators, catalysts, foods, food supplements, nutrients, cosmetics, vitamins, and other agents that benefit the environment of use.

Different environments for use of the osmotic device include biological environments such as the oral, ocular, nasal, vaginal, glands, gastrointestinal tract, rectum, cervical, intrauterine, arterial, venous, otic, sublingual, dermal, epidermal, subdermal, implant, buccal, bioadhesive, mucosal and other similar environments. Likewise, it may be used in aquariums, industrial warehouses, laboratory facilities, hospitals, chemical reactions and other facilities.

Other features, advantages and embodiments of the invention will become apparent to those skilled in the art by the following description, accompanying examples and appended claims.

BRIEF DESCRIPTION OF THE FIGURES

The following drawings are part of the present specification and are included to further demonstrate certain aspects of the invention. The invention may be better understood by reference to one or more of these drawings in combination with the detailed description of the specific embodiments presented herein.

DETAILED DESCRIPTION OF THE INVENTION

Figure 1:
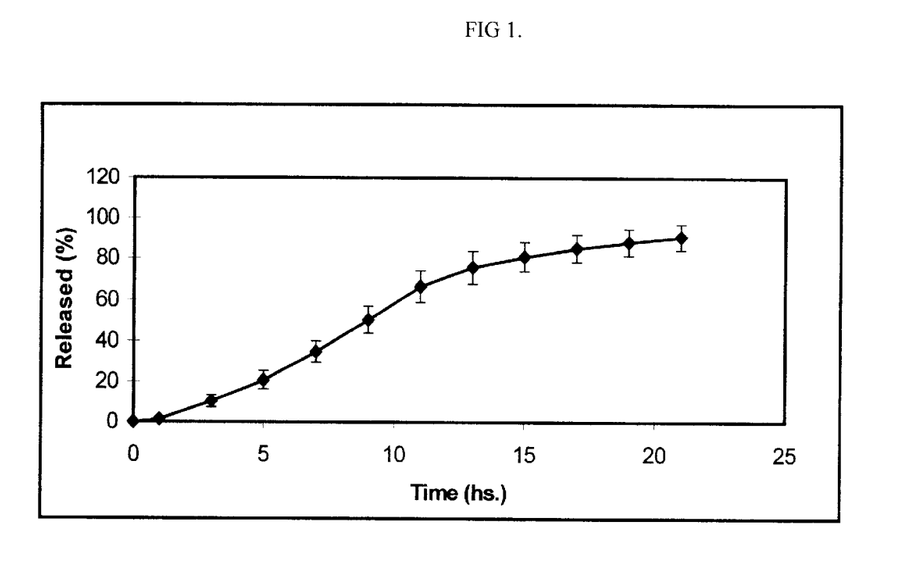
FIG. 1 depicts a release profile of an exemplary formulation of the osmotic device, formed in accordance with Example 1.

Without being held bound to a particular mechanism of operation, it is believed that the osmotic device of the invention produces release profiles as herein described. FIG. 1 depicts a nifedipine in vitro release profile for the osmotic device tablets described in Example 1, the TEC1N-SOL formulation. This profile is an average obtained from several samples.

The release profile for the core of each osmotic device generally resembles a pseudo-first order or first-order release profile. The release profile of the osmotic device of the invention may vary from that shown in FIG. 1 according to the materials used to form the core and the semipermeable covering the core, as well as the method used to form the passageway. For example, the release profile can be influenced by the amount of nifedipine used to form the core, the amount of excipient used to form the core, the type of excipient used to form the core, and the amount or type of any other materials used to form the core such as osmotically effective solutes, osmotic agents, osmopolymers, or osmagents. The release profile can also be influenced by the material used to form the semipermeable membrane covering the core or by the material used to form any coating on the semipermeable membrane. The release profile can also be influenced by whether the preformed passageway increases in size as a result of adjustments made to the means used to form the preformed passageway. The osmotic device of the invention may also have a release profile that generally resembles a pseudo-second order, a second order, a pseudo-third order, or a third order release profile. The upward sigmoidal curvature of the release profile in FIG. 1 indicates an increasing release rate over time.

As shown in FIG. 1, the TEC1N-SOL formulation is generally described as follows:

| Time (h) | Maximum Percent Released | Minimum Percent Released |
|---|---|---|
| 1 | 1.2 | 0.2 |
| 3 | 4.0 | 2.4 |
| 5 | 7.0 | 5.6 |
| 7 | 11.6 | 9.7 |
| 9 | 16.8 | 14.5 |
| 11 | 21.9 | 19.5 |
| 13 | 24.9 | 22.5 |
| 15 | 26.6 | 24.5 |
| 17 | 27.9 | 26.0 |
| 19 | 28.9 | 27.1 |
| 21 | 29.7 | 27.9 |
| 24 | 30.5 | 29.7 |

The nifedipine release profile for the exemplary formulation in Example 1 can also be described as follows (STD indicates standard deviation):

| Time (h) | Avg. Amount Released (%) | STD (%) |
|---|---|---|
| 1 | 0.4 | 0.4 |
| 3 | 3.0 | 0.6 |
| 5 | 6.3 | 0.6 |
| 7 | 10.8 | 0.9 |
| 9 | 15.8 | 0.9 |
| 11 | 20.9 | 0.9 |
| 13 | 23.9 | 0.9 |
| 15 | 25.8 | 0.9 |
| 17 | 27.2 | 0.8 |
| 19 | 28.2 | 0.8 |
| 21 | 29.0 | 0.8 |
| 24 | 30.0 | 0.4 |

Figure 2:
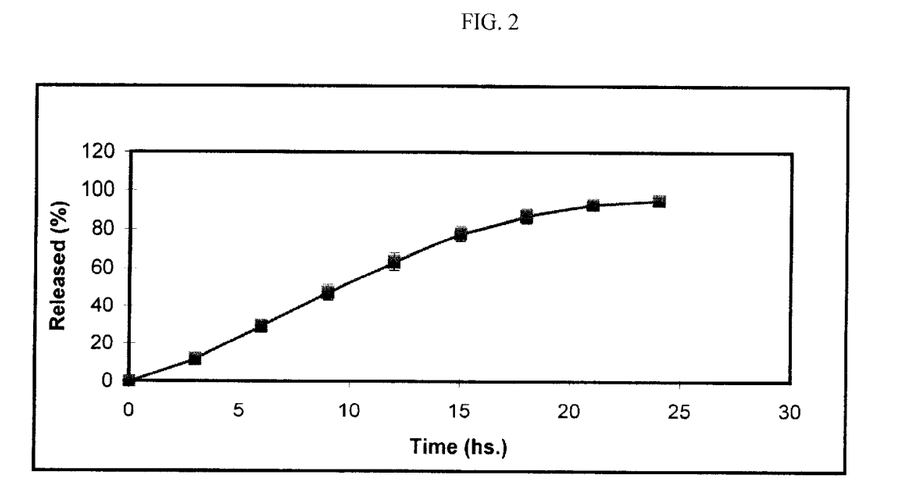
FIG. 2 depicts a drug release profile as provided by a commercial product.

FIG. 2. depicts the nifedipine in vitro release profile of the commercially available product called ADALAT™. By comparing the release profiles of the TEC1N-SOL and the ADALAT™ formulations, it is observed that the formulation of the invention provides an increase in the rate of release of nifedipine; whereas, the ADALAT™ device does not.

Figure 3:
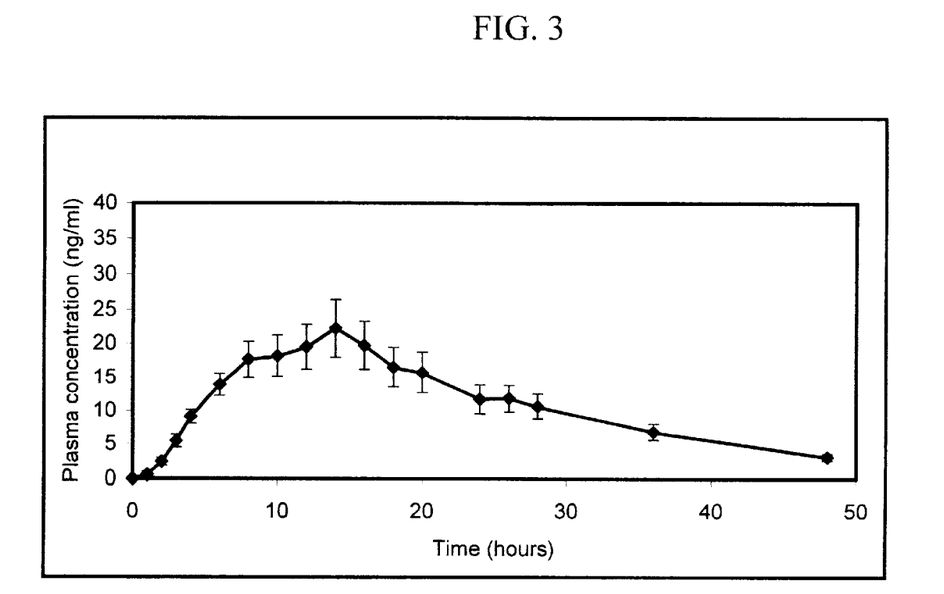
FIG. 3 depicts a plasma profile of an exemplary formulation of the osmotic device prepared according to Example 1.

FIG. 3 is an exemplary plasma profile of an osmotic device tablet formed according to the formulation of Example 1. The plasma profile depicts the pharmacokinetic behavior over time of a drug delivered by the osmotic device of the invention. FIG. 3 indicates that the plasma concentration rose sharply for approximately 9 hours, then peaked gradually over approximately 6 hours to a high concentration of approximately 23 ng/ml. The plasma profile of the osmotic device of the invention can vary from that shown in FIG. 3 for the reasons detailed above regarding FIG. 1.

The nifedipine plasma profile for the exemplary formulation in Example 1 can be described as follows:

| PK Parameter | TEC 1N SOL |
|---|---|
| $AUC_t$ (ng·h/ml) | 522.0 ± 78.8 |
| $AUC_{0\text{-}inf}$ (ng·h/ml) | 587 ± 83.5 |
| Cmax (ng/ml) | 25.3 ± 4.9 |
| Cmax/AUC ($h^{-1}$) | 0.042 ± 0.003 |
| Tmax (h) | 11.23 ± 1.0 |
| T ½ (h) | 12.3 ± 1.9 |
| Ke ($h^{-1}$) | 0.067 ± 0.007 |

Figure 4:
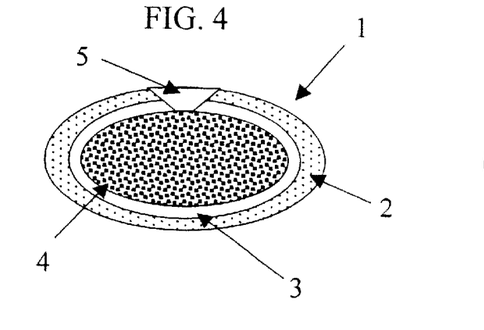
FIG. 4 depicts a sectional side view of an exemplary embodiment of an osmotic device having a passageway that increases in size during use.

Without being held bound to a particular mechanism of operation, it is believed that the osmotic device of the invention delivers one or more active agents to an environment of use as follows. Referring to FIG. 4, the osmotic device (1) comprises a core (4) containing an active agent, an osmopolymer, an osmagent and at least one excipient. The core is surrounded by a semipermeable membrane (3) having a passageway (5) that delivers the active agent to an environment of use in a controlled manner. The optional external coat (2) includes an active agent. The passageway (5) increases from its initial size to a size that allows all or approximately all the active agent to be released. In this embodiment, the preformed passageway (3) extends from the core through to the exterior of the device, since the preformed passageway was formed after the external coat (2) was applied. The osmotic device can provide a release rate of active agent that increases during use. The active agents in the core and external coat can be the same or different.

In particular embodiments, the active agent or an osmotic agent will dissolve or swell in the fluid that enters into the core (4) through the semipermeable membrane (3) thereby creating an osmotic pressure gradient across the semipermeable membrane (3), which gradient provides the force required to push the active agent through the passageway (5) from the core to the exterior of the osmotic device (1). The active agent will continue to be released from the core (4) until osmotic equilibrium between the core and the environment of use is reached. This equilibration of osmotic forces occurs gradually over a period of time thereby serving to control the release of and thus the release profile for the active agent. The release of the active agent slows as osmotic equilibrium is approached, and then stops when osmotic equilibrium is reached. The extent to which the release of the active agent is controlled is known to depend upon a number of other variables such as the permeability of the semipermeable membrane (3) and the magnitude of the osmotic pressure gradient.

Figure 5:
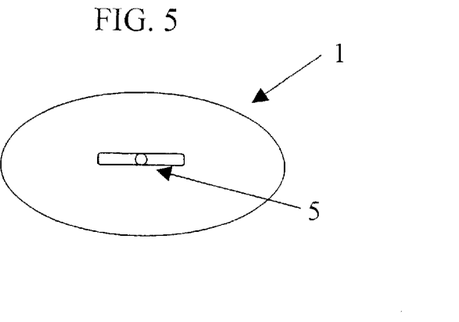
FIG. 5 depicts a top view of the device of FIG. 4.

Although FIG. 5 depicts the osmotic device (1) configured as an oval pill or tablet, it should be understood that the osmotic device can assume any shape or form currently known in the art of osmotic devices. That is, the osmotic device may assume any different shape and/or size according to which are optimal for the intended environment of use. In particular embodiments, the shape and size of the osmotic device will be optimal for use in mammal such as animals or human beings. The device of the invention can be a pill, sphere, tablet, bar, plate, granule, agglomerate or others known to those of ordinary skill. The osmotic device can also include surface markings, cuttings, grooves, letters and/or numerals for the purposes of decoration, identification and/or other purposes.

Figures 6, 8:
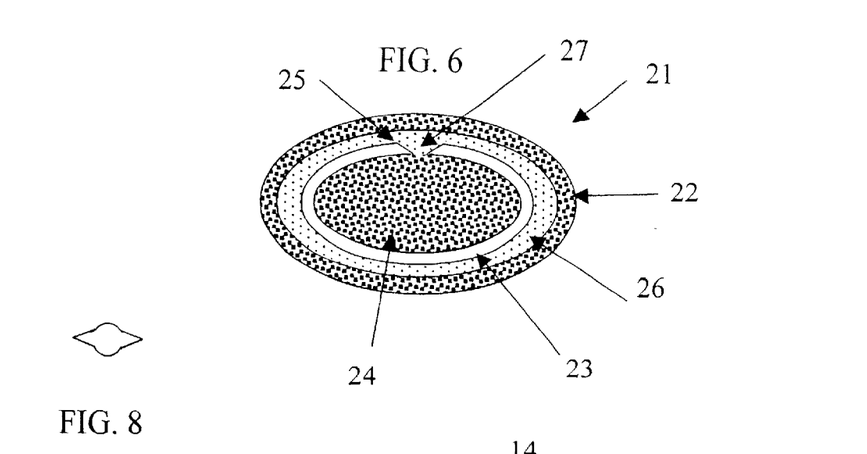
FIG. 6 depicts a sectional side view of an alternative embodiment of an osmotic device having a passageway that increases in size during use, wherein a plug blocks the passageway.
FIG. 8 depicts a top plan view of an exemplary preformed passageway after it has increased size.

When used as a drug delivery device, the osmotic device of the invention can operate as follows provided the right combination of materials is used to formulate the various coatings, the membrane and the core of the osmotic device. FIG. 6 illustrates an alternate embodiment of the invention wherein a polymer coat (26) has been added to form a plug (27) in the preformed passageway (25). In this embodiment, the core has been coated with a semipermeable membrane, which was then perforated by mechanical means, such as a laser, to form the preformed passageway (25). The inert water soluble polymer coat (26) was then applied to the semipermeable membrane (23) to form the plug (27). The external coat (22), which may contain an optional second active agent, was then applied to the polymer coat (26). Following administration to a mammal, the acid soluble, erodible and/or swellable external coat (22) begins to dissolve, erode, swell and/or detach from the osmotic device thereby releasing any second active agent contained therein into the stomach. As the osmotic device (21) moves through the GI tract, portions of the external coat (22) will have partially or completely dissolved, eroded or become detached, thereby exposing the polymer coat (26), which in some embodiments is not soluble in acidic gastric juices. The polymer coat (26) then dissolves or erodes in one or more regions of the intestines according to the particular materials that comprise the polymer coat (26). For example, materials that are soluble in fluids having a pH of 4–6 will dissolve in the small intestine, whereas materials that dissolve in fluids having a pH of 7–8 will dissolve in the large intestine or colon. Combinations of these materials can be used. The polymer coat (26) can also be microporous to permit absorption of water into the core (24) of the osmotic device (21) without dissolution of the polymer coat (26). Once the polymer coat (26) has dissolved or eroded or once at least the plug (27) of the polymer coat (26) has dissolved or eroded, the core (24) will begin to release the first active agent through the passageway (25) into the intestines. The various coatings surrounding the semipermeable membrane can be compression coatings or sprayed-on coatings.

As the first active agent is released through the passageway (25), the passageway (25) increases from its initial size to a size that is 0.1 to 100 times, generally 0.1–10 times of its initial size. The passageway expands in size over time regardless of the plug (27) formed by the polymeric coat (26) that blocks all or part of the passageway (25). The increase in size of the passageway (25) can be 10%, 25%, 50%, 75%, 100%, or more, depending upon the materials used to form the semipermeable membrane and the core.

When a soluble plug (27) temporarily blocks all or a part of the passageway prior to use of the osmotic device, the polymeric coat (26) covering the semipermeable membrane (23) and blocking the passageway (25) is made of synthetic or natural material which, through selective dissolution or erosion shall allow the passageway to be unblocked thus allowing the process of osmotic delivery to start. This slow or fast dissolving polymer coat (26) can be impermeable to a first external fluid, while being soluble in a second external fluid. This property can help to achieve a controlled and selective release of the active compound in the nucleus.

The polymer coat (26) will generally comprise an inert and non-toxic material which is at least partially, and generally substantially completely, soluble or erodible in an environment of use. The polymer coat (26) can be soluble in one or more environments of use. For example, the polymer coat (26) can be soluble in the same environment of use in which the external coat (22) is soluble in, or it can be soluble in the same environment of use in which the core (25) is soluble. Although the art discloses microporous layers comprising materials which can be included in the polymer coat (26), the presence of poly(vinylpyrrolidone)-(vinyl acetate) copolymer in the polymer coat (26) has been found to provide advantageous properties and characteristics to the polymer coat. Thus, the polymer coat (26) will, in some embodiments, comprise poly(vinylpyrrolidone)-(vinyl acetate) copolymer, and it can also include other water soluble materials useful for this type of coat. Exemplary materials are disclosed in U.S. Pat. Nos. 4,576,604 and 4,673,405, and the text Pharmaceutical Dosage Forms: Tablets Volume I, Second Edition. A. Lieberman. ed. 1989, Marcel Dekker, Inc. the relevant disclosures of which are hereby incorporated by reference.

In preferred embodiments, the polymer coat (26) will be insoluble in the fluid of a first environment of use, such as gastric juices, acidic fluids, or polar liquids, and soluble or erodible in the fluid of a second environment of use, such as intestinal juices, substantially pH neutral or basic fluids, or apolar liquids. A wide variety of other polymeric materials are known to possess these various solubility properties and can be included in the polymer coat (26). Such other polymeric materials include, by way of example and without limitation, cellulose acetate phthalate (CAP), cellulose acetate trimelletate (CAT), poly(vinyl acetate) phthalate (PVAP), hydroxypropyl methylcellulose phthalate (HPMCP), poly(methacrylate ethylacrylate) (1:1) copolymer (MA-EA), poly(methacrylate methylmethacrylate) (1:1) copolymer (MA-MMA), poly(methacrylate methylmethacrylate) (1:2) copolymer, Eudragit L-30-D™ (MA-EA, 1:1), Eudragit L-100–55™ (MA-EA, 1:1), hydroxypropyl methylcellulose acetate succinate (HPMCAS), Coateric™ (PVAP), Aquateric™ (CAP), AQUACOAT™ (HPMCAS) and combinations thereof. The polymer coat (26) can also comprise dissolution aids, stability modifiers, and bioabsorption enhancers.

When the polymer coat (26) is intended to be dissolved, eroded or become detached from the core in the colon, materials such as hydroxypropylcellulose, microcrystalline cellulose (MCC, Avicel™ from FMC Corp.), poly (ethylene-vinyl acetate) (60:40) copolymer (EVAC from Aldrich Chemical Co.), 2-hydroxyethylmethacrylate (HEMA), MMA, terpolymers of HEMA: MMA:MA synthesized in the presence of N,N'-bis (methacryloyloxyethyloxycarbonylamino)-azobenzene, azopolymers, enteric coated timed release system (Time Clock® from Pharmaceutical Profiles, Ltd., UK) and calcium pectinate can be included in the polymer coat (6).

A preferred polymeric material for use in the polymer coat (26) involves enteric materials that resist the action of gastric fluid avoiding permeation through the semipermeable wall while one or more of the materials in the core (25) are solubilized in the intestinal tract thereby allowing delivery of a drug in the core (25) by osmotic pumping to begin. A material that easily adapts to this kind of requirement is a poly(vinylpyrrolidone)-vinyl acetate copolymer, such as the material supplied by BASF under its Kollidon VA64 trademark, mixed with magnesium stearate and other similar excipients. The polymer coat (26) can also comprise povidone, which is supplied by BASF under its Kollidon K 30 trademark, and hydroxypropyl methylcellulose, which is supplied by Dow under its Methocel E-15 trademark. The materials can be prepared in solutions having different concentrations of polymer according to the desired solution viscosity. For example, a 10% P/V aqueous solution of Kollidon K 30 has a viscosity of about 5.5–8.5 cps at 20° C., and a 2% P/V aqueous solution of Methocel E-15 has a viscosity of about 13–18 cps at 20° C.

The polymer coat (26) can also comprise other materials suitable which are substantially resistant to gastric juices and which will promote either enteric or colonic release. For this purpose, the polymer coat (26) can comprise one or more materials that do not dissolve, disintegrate, or change their structural integrity in the stomach and during the period of time that the osmotic device (21) resides in the stomach. Representative materials that keep their integrity in the stomach can comprise a member selected from the group consisting of (a) keratin, keratin sandarac-tolu, salol (phenyl salicylate), salol beta-naphthylbenzoate and acetotannin, salol with balsam of Peru, salol with tolu, salol with gum mastic, salol and stearic acid, and salol and shellac; (b) a member selected from the group consisting of formalized protein, formalized gelatin, and formalized cross-linked gelatin and exchange resins; (c) a member selected from the group consisting of myristic acid-hydrogenated castor oil-cholesterol, stearic acid-mutton tallow, stearic acid-balsam of tolu, and stearic acid-castor oil; (d) a member selected from the group consisting of shellac, ammoniated shellac, ammoniated shellac-salol, shellac-wool fat, shellac-acetyl alcohol, shellac-stearic acid-balsam of tolu, and shellac n-butyl stearate; (e) a member selected from the group consisting of abietic acid, methyl abictate, benzoin, balsam of tolu, sandarac, mastic with tolu, and mastic with tolu, and mastic with acetyl alcohol; (f) acrylic resins represented by anionic polymers synthesized from methacrylate acid and methacrylic acid methyl ester, copolymeric acrylic resins of methacrylic and methacrylic acid and methacrylic acid alkyl esters, copolymers of alkylacrylic acid and alkylacrylic acid alkyl esters, acrylic resins such as dimethylaminoethylmethacrylate-butylmethacrylate-methylmethacrylate copolymer of 150,000 molecular weight, methacrylic acid-methylmethacrylate 50:50 coplomer of 135,000 molecular weight, methacrylic acid-methylmethacrylate-30:70-copolymer of 135,000 mol. wt., methacrylic acid-dimethylaminoethyl-methacrylate-ethylacrylate of 750,000 mol. wt., methacrylic acid-methylmethacrylate-ethylacrylate of 1,000,000 mol. wt., and ethylacrylate-methylmethacrylate-ethylacrylate of 550,000 mol. wt; and, (g) an enteric composition comprising a member selected from the group consisting of cellulose acetyl phthalate, cellulose diacetyl phthalate, cellulose triacetyl phthalate, cellulose acetate phthalate, hydroxypropyl methylcellulose phthalate, sodium cellulose acetate phthalate, cellulose ester phthalate, cellulose ether phthalate, methylcellulose phthalate, cellulose ester-ether phthalate, hydroxypropyl cellulose phthalate, alkali salts of cellulose acetate phthalate, alkaline earth salts of cellulose acetate phthalate, calcium salt of cellulose acetate phthalate, ammonium salt of hydroxypropyl methylcellulose phthalate, cellulose acetate hexahydrophthalate, hydroxypropyl methylcellulose hexahydrophthalate, polyvinyl acetate phthalate diethyl phthalate, dibutyl phthalate, dialkyl phthalate wherein the alkyl comprises from 1 to 7 straight and branched alkyl groups, aryl phthalates, and other materials known to one or ordinary skill in the art.

As used herein, the term "preformed passageway" refers to a passageway or passageway precursor that has been formed on the semipermeable membrane by mechanical means, such as by a laser, drill and/or etching apparatus. A preformed passageway is optionally plugged after initial formation, such as depicted in FIG. 6. If a water soluble plug is used, the preformed passageway will increase in size even after all of the plug has been removed from the preformed passageway. The term "preformed passageway" is not intended to cover pores, holes, apertures, channels or other similar structures formed in the semipermeable membrane by incorporation of pore formers, water soluble particulates, or similar materials known to those of ordinary skill, into the semipermeable membrane during manufacture of the osmotic device. The invention does include, however, an osmotic device having a preformed passageway and one or more other pores, holes apertures, channels or other similar structures known to those of ordinary skill.

In an alternate embodiment, plasticizers can be included in the present osmotic device to create additional passageways or to aid in increasing the size of the preformed passageway in a respective coating or membrane, and/or to modify the properties and characteristics of the polymers used in the coats or core of the device. As used herein, the term "plasticizer" includes all compounds capable of plasticizing or softening a polymer or binder used in invention. The plasticizer should be able to lower the melting temperature or glass transition temperature (softening point temperature) of the polymer or binder. Plasticizers, such as low molecular weight PEG, generally broaden the average molecular weight of a polymer in which they are included thereby lowering its glass transition temperature or softening point. Plasticizers also generally reduce the viscosity of a polymer. It is possible the plasticizer will impart some particularly advantageous physical properties to the osmotic device of the invention.

Plasticizers useful in the invention can include, by way of example and without limitation, low molecular weight polymers, oligomers, copolymers, oils, small organic molecules, low molecular weight polyols having aliphatic hydroxyls, ester-type plasticizers, glycol ethers, poly (propylene glycol), multi-block polymers, single block polymers, low molecular weight poly(ethylene glycol), citrate ester-type plasticizers, triacetin, propylene glycol and glycerin. Such plasticizers can also include ethylene glycol, 1,2-butylene glycol, 2,3-butylene glycol, styrene glycol, diethylene glycol, triethylene glycol, tetraethylene glycol and other poly(ethylene glycol) compounds, monopropylene glycol monoisopropyl ether, propylene glycol monoethyl ether, ethylene glycol monoethyl ether, diethylene glycol monoethyl ether, sorbitol lactate, ethyl lactate, butyl lactate, ethyl glycolate, dibutylsebacate, acetyltributylcitrate, triethyl citrate, acetyl triethyl citrate, tributyl citrate and allyl glycolate. All such plasticizers are commercially available from sources such as Aldrich or Sigma Chemical Co. It is also contemplated and within the scope of the invention, that a combination of plasticizers may be used in the present formulation. The PEG based plasticizers are available commercially or can be made by a variety of methods, such as disclosed in *Poly(ethylene glycol) Chemistry: Biotechnical and Biomedical Applications* (J. M. Harris, Ed.; Plenum Press, NY) the disclosure of which is hereby incorporated by reference.

An alternative embodiment of the invention includes pore former(s) in the semipermeable membrane to form additional passageways over time.

The osmotic device (1) will deliver one or more active agents from the core and/or from the external coating, in a controlled manner, and mechanisms employed for such controlled delivery can include active agent release that is pH-dependent or pH-independent; diffusion or dissolution controlled; pseudo-zero order, zero-order, pseudo-first order, first-order or second-order; or rapid, slow, delayed, timed or sustained release or otherwise controlled release.

The external coat is comprised of one or more coatings, which are generally independently selected at each occurrence from the group consisting of: a drug-containing coating, a release rate modifying coating, a porous coating; a soluble coating, an insoluble coating, a semipermeable membrane; and a delayed release coating.

In an alternate embodiment, the external coat (22) may contain a second active agent that may or may not be the same as a first active agent in the core (24). Depending on the composition of the external coat, the second active agent is available for immediate, slow, delayed, sustained, pseudo-first order, pseudo-zero order, timed, controlled release or combinations thereof. The second active agent can be applied to the surface of the device according to common methods of preparing similar osmotic devices which are known to those of ordinary skill such as applying to its surface solids in solution or suspension through the use of a sprayer that spreads them uniformly over the core or by employing nucleated compression or other suitable methods known to those of ordinary skill in the art. The external coat can comprise poly(vinylpyrrolidone) (PVP) and poly (ethylene glycol) (PEG) and can further comprise materials such as, by way of example and without limitation, hydroxypropyl methylcellulose (HPMC), ethylcellulose (EC), hydroxyethylcellulose (HEC), sodium carboxymethylcellulose (CMC), dimethylaminoethyl methacrylate-methacrylic acid ester copolymer, ethylacrylate-methylmethacrylate copolymer (GA-MMA), C-5 or 60 SH-50 (Shin-Etsu Chemical Corp.) and combinations thereof. The active agent-containing external coat (22) can also comprise dissolution aids, stability modifiers, and bioabsorption enhancers.

When the external coat (22) comprises a combination of materials, the relative amounts and ratios of those materials can be varied as desired. For example, when the external coat (22) comprises PVP and PEG, the ratio of PVP:PEG will generally range from about 3–60% by weight of PVP: about 0.1–30% by weight of PEG based upon the weight of the external coat.

The external coat (22) can also comprise a second active agent generally present in an amount ranging from about 0.1 to 99% by weight of the coat. This wide range provides great latitude in the design and application of the osmotic device. Those of ordinary skill in the art will appreciate that the particular amount of second active agent employed will vary according to, among other things, the identity and physical properties and characteristics of the second active agent, the intended application of the osmotic device, the desired effect the second active agent is intended to have, and the physiological condition, if any, being treated.

The preformed passageway (5) in the semipermeable wall is generated by mechanical means, such as perforation by a laser or drill, or any other similar method known to those of ordinary skill in the art. The passageway is generally formed by controlled laser perforation, using an apparatus similar to that disclosed in Theeuwes et al. '864, the entire disclosure of which is incorporated herein by reference. Specific embodiments of the controlled laser perforation method will vary according to the equipment used. The laser equipment of Theeuwes et al. '864 can be modified as described herein to prepare an osmotic device according to the invention. For example, the laser pulse width and pulse period can be varied, as can the total exposure time of an osmotic device to the laser, and as can the linear velocity of an osmotic device travelling under the path of the laser pulse. Other suitable laser equipment, are methods of use thereof, are disclosed in Emerton et al. '793 and Roy '771, the entire disclosures of which are hereby incorporated by reference.

According to one embodiment of the invention, at least one coated core is moved along a predetermined path in a laser apparatus at a predetermined linear velocity that is greater than the velocity used to make similar osmotic devices that do not have passageways that increase in size during use. The coated core is tracked at the predetermined velocity with a laser having a wavelength that is absorbable by the coating. During the tracking, a laser beam, which comprises sequential individual pulses, is then fired at a predetermined section of the coated core for a predetermined period of time and with a predetermined pulse period. The pulse period is the period of time measured from the beginning of a first individual pulse to the beginning of the next individual pulse of the laser beam. The laser beam is also adjusted to fire with a predetermined pulse width, which is the amount of time from the beginning of an individual pulse to the end of that same individual pulse. By controlling the three pulse parameters and the liner velocity, passageways as depicted in FIG. 7 can be prepared.

Figure 7:
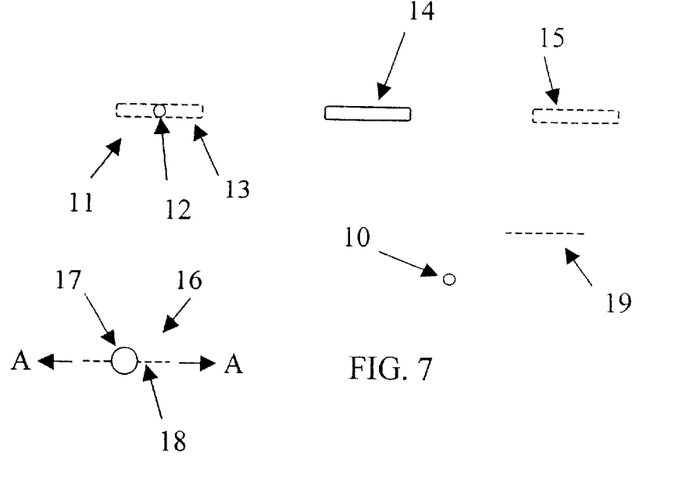
FIG. 7 depicts various alternate embodiments for an aperture according to the invention.

Preformed passageways of different sizes, shapes and functions, such as those depicted in FIG. 7 can be formed. The passageway (11) includes a central circular hole (12) that penetrates the semipermeable membrane, and two laterally extending portions (13), which are scored, or etched, regions, that do not penetrate the semipermeable membrane. When this passageway is used, the semipermeable membrane tears or dissolves along the etched regions to form the enlarged preformed passageway. The laterally extending regions can be any length desired. The passageway (14) is oval- or slot-shaped, and it penetrates the semipermeable membrane. When it is used, the preformed passageway will generally tend to tear at the ends of the slot. The passageway (15) is scored on the surface of the semipermeable membrane. The scored region (15) ruptures during use to form the actual passageway through which active agent is released. This preformed passageway can continue to tear along the direction of the score or it can tear in random directions. The passageway (16) is similar to the passageway (11) except that these scored regions (18) have a much narrower width and depth than the other scored regions (13). The passageway (19) is actually a scored region on the semipermeable membrane that ruptures during use of the osmotic device. The passageways (10, 11, 14, 15, 16, and 19) are generally formed with a laser. The passageways (11, 14, 15, 16, and 19) will generally increase in size in a predetermined manner during use, i.e., generally in a direction extending along the lateral axes of the passageways. FIG. 8 depicts a preformed passageway, such as one of those depicted in FIG. 7, after it has increased in sized. Accordingly, the preformed passageway does not require etchings or scored regions at its edge in order to increase in size during use.

The passageway (5) formed in the semipermeable membrane (3) may dissolve or tear in a predetermined or random manner, and the shape of the preformed passageway after enlargement can be made to approximate a predetermined or randomly determined shape.

The extent to which the passageway (5) increases in size can also be related to the viscosity, molecular weight or degree of substitution of the at least one excipient. Generally, increasing the viscosity, molecular weight, or degree of substitution of the at least one excipient will increase the extent to which the passageway increases in size. Rupture of the semipermeable membrane in areas adjacent the preformed passageway effects an increase in the size of the passageway. This rupture can be due to excessive internal osmotic pressure buildup in combination with an undersized preformed passageway and/or a thin, weak or brittle semipermeable membrane. For example, a core exhibiting an extremely high osmotic pressure during use can be used in combination with a small preformed passageway having an optional scored region adjacent the preformed passageway. By making the semipermeable membrane thin, weak or brittle, it will rupture in a region adjacent the preformed passageway thereby effecting an increase in the size of the passageway.

Although the osmotic device (1) is depicted with a single preformed passageway (5), a device according to the present invention can comprise one or more preformed passageways including two, three, four, five, six, seven, eight, nine, ten or more preformed passageways. It is only necessary that at least one of the preformed passageways increase in size during use.

Many common materials known by those of ordinary skill in the art are suitable for use as the semipermeable membrane. Exemplary materials include cellulose esters, cellulose ethers and cellulose esters-ethers. However, it has been found that a semipermeable membrane consisting essentially of cellulose acetate (CA) and poly(ethylene glycol) (PEG), in particular PEG 400, is preferred when used in combination with the other materials required in the present osmotic device. This particular combination of CA and PEG provides a semipermeable membrane that gives the osmotic device a well controlled release profile for the active agent in the core and that retains its chemical and physical integrity in the environment of use. The ratio of CA:PEG generally ranges from about 50–99% by weight of CA: about 50–1% by weight of PEG, and generally about 95% by weight of CA: about 5% by weight of PEG. The ratio can be varied to alter permeability and ultimately the release profile of the osmotic device. Other preferred materials can include a selected member of the group of cellulose acylates such as cellulose acetate, cellulose diacetate, cellulose triacetate and combinations thereof. Many suitable polymers, include those disclosed in Argentine Patent No. 199,301 and other references cited herein, the disclosures of which are hereby incorporated by reference.

The core (4) of the osmotic device of the present invention will comprise an active agent and an osmotic agent and can further comprise many other materials as discussed herein. The amount of active agent present can vary as described above for the external coat (2). Generally, the active agent will be present in an amount ranging from 0.1–99.9% by weight of the uncoated core (4). Specific ranges will vary according to the active agent used and the intended use of the osmotic device.

When the active agent is of limited solubility in the environment of use, osmotically effective solutes or osmotic agents, i.e. osmagents, that are capable of being totally or partially solubilized in the fluid, are added. These osmagents will aid in either the suspension or dissolution of the active agent in the core. Exemplary osmagents include organic and inorganic compounds such as salts, acids, bases, chelating agents, sodium chloride, lithium chloride, magnesium chloride, magnesium sulfate, lithium sulfate, potassium chloride, sodium sulfite, calcium bicarbonate, sodium sulfate, calcium sulfate, calcium lactate, d-mannitol, urea, tartaric acid, raffinose, sucrose, alpha-d-lactose monohydrate, glucose, combinations thereof and other similar or equivalent materials which are widely known in the art.

These osmagents can also be incorporated to the core of the osmotic device to control the release of an active agent therein. When the agent is only partially or incompletely soluble in the fluid of an environment of use, it can be released as a suspension provided sufficient fluid has been imbibed or absorbed by the core to form a suspension.

One or more osmopolymers can also be added to the core of the device to aid in the delivery of active agents. Osmopolymers are well known to those of ordinary skill in the osmotic device art and well described in the patent and scientific literature. Exemplary osmopolymers include hydrophilic polymers that swell upon contact with water. Osmopolymers may be of plant or animal origin, or synthetic. Examples of osmopolymers include: poly(hydroxyalkyl methacrylates) with molecular weight of 30,000 to 5,000,000, poly(vinylpyrrolidone) with molecular weight of 10,000 to 360,000, anionic and cationic hydrogels, polyelectrolyte complexes, poly(vinyl alcohol) having low acetate residual, optionally cross-linked with glyoxal, formaldehyde or glutaraldehyde and having a degree of polymerization of 200 to 30,000, a mixture of methyl cellulose, cross-linked agar and carboxymethylcellulose, a mixture of hydroxypropyl methylcellulose and sodium carboxymethylcellulose, polymers of N-vinyllactams, polyoxyethylene-polyoxypropylene gels, polyoxybutylene-polyethylene block copolymer gels, carob gum, polyacrylic gels, polyester gels, polyurea gels, polyether gels, polyamide gels, polypeptide gels, polyamino acid gels, polycellulosic gels, carbopol acidic carboxy polymers having molecular weights of 250,000 to 4,000,000, Cyanamer polyacrylamides, cross-linked indene-maleic anhydride polymers, Good-Rite™ polyacrylic acids having molecular weights of 80,000 to 200,000, Polyox™ polyethylene oxide polymers having molecular weights of 100,000 to 5,000,000, starch graft copolymers, and Aqua-Keeps™ acrylate polymer polysaccharides. These materials swell or expand to an equilibrium state when exposed to water or other biological fluids. This volume expansion is used to physically force the pharmaceutical agent out through openings that have been formed in the wall, shell or coating during manufacture. A water insoluble active agent is primarily released as insoluble particles, which therefore have limited bioavailability. Exemplary osmopolymers are disclosed in U.S. Pat. Nos. 5,422,123; 4,783,337; 4,765,989; 4,612,008; 4,327,725; 4,609,374; 4,036,228; 4,992,278; 4,160,020; 4,615,698. The osmopolymers generally swell or expand to a very high degree, usually exhibiting a 2 to 60 fold volume increase. The osmopolymers can be non-cross-linked or cross-linked. The swellable, hydrophilic polymers are, in one embodiment, lightly cross-linked, such as cross-links being formed by covalent or ionic bonds.

As used herein, the term brittling agent refers to a compound or composition that renders the semipermeable membrane more susceptible to rupture during use thereby facilitating increasing the size of the preformed passageway.

The osmotic device of the invention can also comprise adsorbents, antioxidants, buffering agents, colorants, flavorants, sweetening agents, tablet antiadherents, tablet binders, tablet and capsule diluents, tablet direct compression excipients, tablet disintegrants, tablet glidants, tablet lubricants, tablet or capsule opaquants and/or tablet polishing agents.

As used herein, the term "adsorbent" is intended to mean an agent capable of holding other molecules onto its surface by physical or chemical (chemisorption) means. Such compounds include, by way of example and without limitation, powdered and activated charcoal and other materials known to one of ordinary skill in the art.

As used herein, the term "antioxidant" is intended to mean an agent that inhibits oxidation and thus is used to prevent the deterioration of preparations by the oxidative process. Such compounds include, by way of example and without limitation, ascorbic acid, ascorbyl palmitate, butylated hydroxyanisole, butylated hydroxytoluene, hypophophorous acid, monothioglycerol, propyl gallate, sodium ascorbate, sodium bisulfite, sodium formaldehyde sulfoxylate and sodium metabisulfite and other materials known to one of ordinary skill in the art.

As used herein, the term "buffering agent" is intended to mean a compound used to resist change in pH upon dilution or addition of acid or alkali. Such compounds include, by way of example and without limitation, potassium metaphosphate, potassium phosphate, monobasic sodium acetate and sodium citrate anhydrous and dihydrate and other materials known to one of ordinary skill in the art.

As used herein, the term "sweetening agent" is intended to mean a compound used to impart sweetness to a preparation. Such compounds include, by way of example and without limitation, aspartame, dextrose, glycerin, mannitol, saccharin sodium, sorbitol and sucrose and other materials known to one of ordinary skill in the art.

As used herein, the term "tablet antiadherents" is intended to mean agents which prevent the sticking of tablet formulation ingredients to punches and dies in a tableting machine during production. Such compounds include, by way of example and without limitation, magnesium stearate, talc, calcium stearate, glyceryl behenate, PEG, hydrogenated vegetable oil, mineral oil, stearic acid and other materials known to one of ordinary skill in the art.

As used herein, the term "tablet binders" is intended to mean substances used to cause adhesion of powder particles in table granulations. Such compounds include, by way of example and without limitation, acacia, alginic acid, carboxymethylcellulose sodium, poly(vinylpyrrolidone), compressible sugar (e.g., NuTab™), ethylcellulose, gelatin, liquid glucose, methylcellulose, povidone and pregelatinized starch and other materials known to one of ordinary skill in the art.

When needed, binders may also be included in the present osmotic device. Exemplary binders include acacia, tragacanth, gelatin, starch, cellulose materials such as methyl cellulose and sodium carboxy methyl cellulose, alginic acids and salts thereof, polyethylene glycol, guar gum, polysaccharide, bentonites, sugars, invert sugars, poloxamers (PLURONIC F68, PLURONIC F127), collagen, albumin, gelatin, cellulosics in nonaqueous solvents, combinations thereof and others known to those of ordinary skill. Other binders include, for example, polypropylene glycol, polyoxyethylene-polypropylene copolymer, polyethylene ester, polyethylene sorbitan ester, polyethylene oxide, combinations thereof and other materials known to one of ordinary skill in the art.

As used herein, the term "tablet and capsule diluent" or "fillers" is intended to mean inert substances used as fillers to create the desired bulk, flow properties, and compression characteristics in the preparation of tablets and capsules. Such compounds include, by way of example and without limitation, dibasic calcium phosphate, kaolin, lactose, sucrose, mannitol, microcrystalline cellulose, powdered cellulose, precipitated calcium carbonate, sorbitol, and starch and other materials known to one of ordinary skill in the art.

As used herein, the term "tablet direct compression excipient" is intended to mean a compound used in direct compression tablet formulations. Such compounds include, by way of example and without limitation, dibasic calcium phosphate (e.g., Ditab) and other materials known to one of ordinary skill in the art.

As used herein, the term "tablet glidant" is intended to mean agents used in tablet and capsule formulations to promote the flowability of a granulation. Such compounds include, by way of example and without limitation, colloidal silica, cornstarch, talc, calcium silicate, magnesium silicate, colloidal silicon, silicon hydrogel and other materials known to one of ordinary skill in the art.

As used herein, the term "tablet lubricant" is intended to mean substances used in tablet formulations to reduce friction during tablet compression. Such compounds include, by way of example and without limitation, calcium stearate, magnesium stearate, mineral oil, stearic acid, and zinc stearate and other materials known to one of ordinary skill in the art.

As used herein, the term "tablet/capsule opaquant" is intended to mean a compound used to render a capsule or a tablet coating opaque. May be used alone or in combination with a colorant. Such compounds include, by way of example and without limitation, titanium dioxide and other materials known to one of ordinary skill in the art.

As used herein, the term "tablet polishing agent" is intended to mean a compound used to impart an attractive sheen to coated tablets. Such compounds include, by way of example and without limitation, carnauba wax, and white wax and other materials known to one of ordinary skill in the art.

As used herein, the term "tablet disintegrant" is intended to mean a compound used in solid dosage forms to promote the disruption of the solid mass into smaller particles which are more readily dispersed or dissolved. Exemplary disintegrants include, by way of example and without limitation, starches such as corn starch, potato starch, pre-gelatinized and modified starches thereof, sweeteners, clays, such as bentonite, microcrystalline cellulose (e.g., Avicel), carboxymethylcellulose calcium, cellulose polyacrilin potassium (e.g., Amberlite), alginates, sodium starch glycolate, gums such as agar, guar, locust bean, karaya, pectin, tragacanth and other materials known to one of ordinary skill in the art.

As used herein, the term "colorant" is intended to mean a compound used to impart color to solid (e.g., tablets) pharmaceutical preparations. Such compounds include, by way of example and without limitation, FD&C Red No. 3, FD&C Red No. 20, FD&C Yellow No. 6, FD&C Blue No. 2, D&C Green No. 5, D&C Orange No. 5, D&C Red No. 8, caramel, and ferric oxide, red, other F.D. & C. dyes and natural coloring agents such as grape skin extract, beet red powder, beta-carotene, annato, carmine, turmeric, paprika, and other materials known to one of ordinary skill in the art. The amount of coloring agent used will vary as desired.

As used herein, the term "flavorant" is intended to mean a compound used to impart a pleasant flavor and often odor to a pharmaceutical preparation. Exemplary flavoring agents or flavorants include synthetic flavor oils and flavoring aromatics and/or natural oils, extracts from plants, leaves, flowers, fruits and so forth and combinations thereof. These may also include cinnamon oil, oil of wintergreen, peppermint oils, clove oil, bay oil, anise oil, eucalyptus, thyme oil, cedar leave oil, oil of nutmeg, oil of sage, oil of bitter almonds and cassia oil. Other useful flavors include vanilla, citrus oil, including lemon, orange, grape, lime and grapefruit, and fruit essences, including apple, pear, peach, strawberry, raspberry, cherry, plum, pineapple, apricot and so forth. Flavors which have been found to be particularly useful include commercially available orange, grape, cherry and bubble gum flavors and mixtures thereof. The amount of flavoring may depend on a number of factors, including the organoleptic effect desired. Flavors will be present in any amount as desired by those of ordinary skill in the art. Particularly preferred flavors are the grape and cherry flavors and citrus flavors such as orange.

The present osmotic device can also employ one or more commonly known surface active agents or cosolvents that improve wetting or disintegration of the osmotic device core or layers.

It is contemplated that the osmotic device of the invention can also include oils, for example, fixed oils, such as peanut oil, sesame oil, cottonseed oil, corn oil and olive oil; fatty acids, such as oleic acid, stearic acid and isotearic acid; and fatty acid esters, such as ethyl oleate, isopropyl myristate, fatty acid glycerides and acetylated fatty acid glycerides. It can also be mixed with alcohols, such as ethanol, isopropanol, hexadecyl alcohol, glycerol and propylene glycol; with glycerol ketals, such as 2,2-dimethyl-1,3-dioxolane-4-methanol; with ethers, such as poly(ethyleneglycol) 450, with petroleum hydrocarbons, such as mineral oil and petrolatum; with water, or with mixtures thereof; with or without the addition of a pharmaceutically suitable surfactant, suspending agent or emulsifying agent.

Soaps and synthetic detergents may be employed as surfactants and as vehicles for detergent compositions. Suitable soaps include fatty acid alkali metal, ammonium, and triethanolamine salts. Suitable detergents include cationic detergents, for example, dimethyl dialkyl ammonium halides, alkyl pyridinium halides, and alkylamine acetates; anionic detergents, for example, alkyl, aryl and olefin sulfonates, alkyl, olefin, ether and monoglyceride sulfates, and sulfosuccinates; nonionic detergents, for example, fatty amine oxides, fatty acid alkanolamides, and poly(oxyethylene)-block-poly(oxypropylene) copolymers; and amphoteric detergents, for example, alkyl aminopropionates and 2-alkylimidazoline quaternary ammonium salts; and mixtures thereof.

Various other components, not otherwise listed above, can be added to the present formulation for optimization of a desired active agent release profile including, by way of example and without limitation, glycerylmonostearate, nylon, cellulose acetate butyrate, d, 1-poly(lactic acid), 1,6-hexanediamine, diethylenetriamine, starches, derivatized starches, acetylated monoglycerides, gelatin coacervates, poly (styrene-maleic acid) copolymer, glycowax, castor wax, stearyl alcohol, glycerol palmitostearate, poly(ethylene), poly(vinyl acetate), poly(vinyl chloride), 1,3-butylene-glycoldimethacrylate, ethyleneglycol-dimethacrylate and methacrylate hydrogels.

It should be understood, that compounds used in the art of pharmaceutical formulation generally serve a variety of functions or purposes. Thus, if a compound named herein is mentioned only once or is used to define more than one term herein, its purpose or function should not be construed as being limited solely to that named purpose(s) or function(s).

Active agents include physiological substances or pharmacological active substances that produce a systemic or localized effect or effects on animals and human beings. Active agents also include pesticides, herbicides, insecticides, antioxidants, plant growth instigators, sterilization agents, catalysts, chemical reagents, food products, nutrients, cosmetics, vitamins, sterility inhibitors, fertility instigators, microorganisms, flavoring agents, sweeteners, cleansing agents and other such compounds for pharmaceutical, veterinary, horticultural, household, food, culinary, agricultural, cosmetic, industrial, cleansing, confectionery and flavoring applications. The active agent can be present in its neutral, ionic, salt, basic, acidic, natural, synthetic, diastereomeric, isomeric, enantiomerically pure, racemic, hydrate, chelate, derivative, analog, or other common form.

Further therapeutic compounds which can be formulated into the present osmotic devices also include antibacterial substances, antihistamines and decongestants, anti-inflammatories, antiparasitics, antivirals, local anesthetics, antifungal, amoebicidal, or trichomonocidal agents, analgesics, antiarthritics, antiasthmatics, anticoagulants, anticonvulsants, antidepressants, antidiabetics, antineoplastics, antipsychotics, neuroleptics, antihypertensives, muscle relaxants, depressants, hypnotics, sedatives, psychic energizers, tranquilizers, anticonvulsants, antiparkinson agents, muscle contractants, antimicrobials, antimalarials, hormonal agents, contraceptives, sympathomimetics, diuretics, hypoglycemics, ophthalmics, electrolytes, diagnostics agents and cardiovascular drugs.

Representative antibacterial substances are beta-lactam antibiotics, tetracyclines, chloramphenicol, neomycin, gramicidin, bacitracin, sulfonamides, aminoglycoside antibiotics, tobramycin, nitrofurazone, nalidixic acid, penicillin, tetracycline, oxytetracycline, chlorotetracycline, erythromycin, cephalosporins and analogs and the antimicrobial combination of fludalanine/pentizidone. Other representative antibacterial agents include of the poorly water-soluble pyrridone-carboxylic acid type such as benofloxacin, nalidixic acid, enoxacin, ofloxacin, amifloxacin, flumequine, tosfloxacin, piromidic acid, pipemidic acid, miloxacin, oxolinic acid, cinoxacin, norfloxacin, ciprofloxacin, pefloxacin, lomefloxacin, enrofloxacin, danofloxacin, binfloxacin, sarafloxacin, ibafloxacin, difloxacin and salts thereof.

Representative antiparasitic compounds are ivermectin, bephenium, hydroxynaphthoate, dichlorophen and dapsone. Representative anti-malarial compounds are 4-aminoquinolines, 8-aminoquinolines and pyrimethamine.

Representative antiviral compounds are protease inhibitors, neuramidinase inhibitors, commercially available compounds, acyclovir and interferon.

Representative anti-inflammatory drugs include NSAIDS, steroids, cyclooxygenase inhibitors, cortisone, hydrocortisone, betamethasone, dexamethasone, fluocortolone, prednisolone, phenylbutazone, triamcinolone, sulindac and its salts and corresponding sulfide, indomethacin, salicylamide, naproxen, colchicine, fenoprofen, diclofenac, indoprofen, dexamethasone, allopurinol, oxyphenbutazone, probenecid and sodium salicylamide.

Representative analgesic drugs are diflunisal, aspirin, ibuprofen, profen-type compounds, morphine, codeine, meperidine, nalorphine, or acetaminophen.

Representative antihistamines and decongestants are H1 histamine receptor antagonists, perilamine, chlorpheniramine, cimetidine, tetrahydrozoline, loratadine, and antazoline.

Representative antiasthma drugs are theophylline, pseudoephedrine, ephedrine, beclomethasone dipropionate and epinephrine.

Representative anticoagulants are heparin, bishydroxycoumarin, and warfarin.

Representative psychic energizers are isocoboxazid, nialamide, phenelzine, imipramine, tranycypromine, and parglyene.

Representative anticonvulsants are diphenylhydantoin, primidone, enitabas, diphenylhydantion, ethltion, pheneturide, ethosuximide and diazepam.

Representative antidepressants are amitriptyline, chlordiazepoxide perphenazine, protriptyline, imipramine and doxepin.

Representative antidiabetics are insulin, somatostatin and its analogs, tolbutamide, tolazamide, chlorpropamide, isophane insulin, protamine zinc insulin suspension, globin zinc insulin, extended insulin zinc suspension and acetohexamide.

Representative antineoplastics are adriamycin, fluorouracil, methotrexate, nechlorethamine, uracil mustard, 5-fluorouracil, 6–6-thioguanine and procarbazine asparaginase.

Representative steroidal drugs are prednisolone, cortisone, cortisol and triamcinolone; androgenic steroids such as methyltesterone, and fluoxmesterone; estrogenic steroids such as 17β-estradiol, α-estradiol, estriol, α-estradiol 3 benzoate, and 17-ethynylestradiol-3-methyl ether; progestational steriods such as progesterone, 19-norpregn-4-ene-3,20-dione, 17-hydroxy-19-nor-17-α-pregn-5 (10)-ene-20-yn-3-one, 17α-ethynyl-17-hydroxy-5(10)-estren-3-one, and 9β, 10α-pregna-4,6-diene-3,20-dione.

Representative antipsychotics are prochlorperazine, lithium carbonate, lithium citrate, thioridazine, molindone, fluphenazine, trifluoperazine, perphenazine, amitriptyline and trifluopromazine.

Representative hypnotics and sedatives are pentobarbital sodium, phenobarbital, secobarbital, thiopental, heterocyclic hypnotics, dioxopiperidines, glutarimides, diethylisovaleramide, α-bromoisovaleryl urea, urethanes, disulfanes and mixtures thereof.

Representative antihypertensives are spironolactone, methyldopa, hydralazine, clonidine, chlorothiazide, deserpidine, timolol, propranolol, metoprolol, prazosin hydrochloride, methyl dopa (L-β-3,4-dihydroxyphenylalanine), pivaloyloxyethyl ester of α-methyldopa hydrochloride dihydrate and reserpine.

Representative tranquilizers are chloropromazine, promazine, fluphenazine, reserpine, deserpidine, meprobamate, and benezodiazepines such as chlordiazepoxide.

Representative anti-spasmodics and muscle contractants are atropine, scopolamine, methscopolamine, oxyphenonium, papaverine, and prostaglandins such as $PGE_1$ $PGE_2$ $PGF_{1\alpha}$ $PGF_{2\alpha}$ and PGA.

Representative local anesthetics are benzocaine, procaine, lidocaine, maepaine, piperocaine, tetracaine and dibucaine.

Representative muscle relaxants and anti-Parkinson agents are succinylcholine-chloride, danbrolene, cyclobenzaprine, methocarbamol, diazepam, mephenesin, methocarbomal, trihexylphenidyl, pridinol, and biperiden.

Representative sympathomimetic drugs are epinephrine, amphetamine ephedrine and norepinephrine.

Representative cardiovascular drugs are procainamide, procainamide hydrochloride, amyl nitrite, nitroglycerin, dipyredamole, sodium nitrate and mannitol nitrate.

Representative diuretics are chlorathiazide, acetazolamide, methazolamide and flumethiazide.

Representative β-blockers are pindolol, propranolol, practolol, metoprolol, oxprenolol, timolol, atenolol, alprenolol, and acebutolol.

Representative nutritional agents are ascorbic acid, niacin, nicotinamide, folic acid, choline biotin, panthothenic acid, and vitamin $B_{12}$, essential amino acids; essential fats.

Representative ophthalmic agents are pilocarpine, pilocarpine salts such as pilocarpine nitrate, pilocarpine hydrochloride, dichlophenamide, atropine, atropine sulfate, scopolamine and eserine salicylate.

Representative electrolytes are calcium gluconate, calcium lactate, potassium chloride, potassium sulfate, sodium chloride, potassium fluoride, ferrous lactate, ferrous gluconate, ferrous sulfate, ferrous fumurate and sodium lactate.

Representative drugs that act on α-adrenergic receptors are clonidine hydrochloride.

Other suitable drugs include nimodipine, carbamazepine, tramadol and phenytoin.

The therapeutic compound(s) contained within the present osmotic device can be formulated as its pharmaceutically acceptable salts. As used herein, "pharmaceutically acceptable salts" refer to derivatives of the disclosed compounds wherein the therapeutic compound is modified by making an acid or base salt thereof. Examples of pharmaceutically acceptable salts include, but are not limited to, mineral or organic acid salts of basic residues such as amines; alkali or organic salts of acidic residues such as carboxylic acids; and others known to those of ordinary skill. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfonic, sulfamic, phosphoric, nitric and others known to those of ordinary skill; and the salts prepared from organic acids such as amino acids, acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and others known to those of ordinary skill. The pharmaceutically acceptable salts of the present invention can be synthesized from the parent therapeutic compound which contains a basic or acidic moiety by conventional chemical methods. Lists of suitable salts are found in *Remington's Pharmaceutical Sciences*, 17th ed., Mack Publishing Company, Easton, Pa., 1985, p. 1418, the disclosure of which is hereby incorporated by reference.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used in this disclosure, the term vitamin refers to trace organic substances that are required in the diet. For the purposes of the present invention, the term vitamin(s) include, without limitation, thiamin, riboflavin, nicotinic acid, pantothenic acid, pyridoxine, biotin, folic acid, vitamin B12, lipoic acid, ascorbic acid, vitamin A, vitamin D, vitamin E and vitamin K. Also included within the term vitamin are the coenzymes thereof. Coenzymes are specific chemical forms of vitamins and can include thiamine pyrophosphates (TPP), flavin mononucleotide (FMN), flavin adenine dinucleotive (FAD), Nicotinamide adenine dinucleotide (NAD), Nicotinamide adenine dinucleotide phosphate (NADP), Coenzyme A (CoA), pyridoxal phosphate, biocytin, tetrahydrofolic acid, coenzyme B12, lipoyllysine, 11-cis-retinal, and 1,25-dihydroxycholecalciferol. The term vitamin(s) also includes choline, carnitine, and alpha, beta, and gamma carotenes.

As used in this disclosure, the term "mineral" refers to inorganic substances, metals, and others known to those of ordinary skill required in the human diet. Thus, the term "mineral" as used herein includes, without limitation, calcium, iron, zinc, selenium, copper, iodine, magnesium, phosphorus, chromium and others known to those of ordinary skill, and mixtures thereof.

The term "dietary supplement" as used herein means a substance which has an appreciable nutritional effect when administered in small amounts. Dietary supplements include, without limitation, such ingredients as bee pollen, bran, wheat germ, kelp, cod liver oil, ginseng, and fish oils, amino-acids, proteins, plant extracts, plant powder, herbs, herbal extracts and powders, vitamins, minerals, combinations thereof and others known to those of ordinary skill. As will be appreciated, essentially any dietary supplement may be incorporated into the present osmotic device.

The amount of therapeutic compound incorporated in each osmotic device will be at least one or more unit dose and can be selected according to known principles of pharmacy. An effective amount of therapeutic compound is specifically contemplated. By the term "effective amount", it is understood that, with respect to, for example, pharmaceuticals, a pharmaceutically effective amount is contemplated. A pharmaceutically effective amount is the amount or quantity of a drug or pharmaceutically active substance which is sufficient to elicit the required or desired therapeutic response, or in other words, the amount which is sufficient to elicit an appreciable biological response when administered to a patient. As used with reference to a vitamin or mineral, the term "effective amount" means an amount at least about 10% of the United States Recommended Daily Allowance ("RDA") of that particular ingredient for a patient. For example, if an intended ingredient is vitamin C, then an effective amount of vitamin C would include an amount of vitamin C sufficient to provide 10% or more of the RDA. Typically, where the tablet includes a mineral or vitamin, it will incorporate higher amounts, generally about 100% or more of the applicable RDA.

For nasal, oral, buccal, and sublingual administration, the osmotic device may be in the form of a caplet, tablet or pill. For rectal administration, the osmotic device can be included in a suppository, tablet, implant or patch for release of a therapeutic compound into the intestines, sigmoid flexure and/or rectum.

The term "unit dosage form" is used herein to mean an osmotic device containing a quantity of the therapeutic compound, said quantity being such that one or more predetermined units may be provided as a single therapeutic administration.

The osmotic device of the invention can be prepared according to the methods disclosed herein or those well known in the art. For example, according to one manufacturing technique, the active agent and excipients that comprise the core can be mixed in solid, semisolid or gelatinous form, then moistened and sieved through a specified screen to obtain a granulate. The granulate is then dried in a dryer and compressed, for example, by punching to form uncoated cores. The compressed and uncoated cores (4) are then covered with a solution of suitable materials that comprise the semipermeable membrane (3). Subsequently, the semipermeable membrane (3) surrounding each core is perforated with, for example, laser equipment to form the preformed passageway (5) in the manner previously described. Finally, the active agent-containing external coat (2) is optionally applied.

If desired, the osmotic devices of the invention can be coated with a finish coat as is commonly done in the art to provide the desired shine, color, taste or other aesthetic characteristics. Materials suitable for preparing the finish coat are well known in the art and found in the disclosures of many of the references cited and incorporated by reference herein.

The following examples should not be considered exhaustive, but merely illustrative of only a few of the many embodiments contemplated by the present invention. The methods described herein can be followed to prepare osmotic devices according to the invention.

EXAMPLE 1

The following process is used for the preparation of 30 mg strength Nifedipine-SOL tablets.

In a laboratory mixer/kneader, mix nifedipine (33.00 mg), NaCl (111.70 mg), Tween 20 (1.40 mg), Avicel pH 101 (30.00 mg), P.V.P. (50.00 mg), poly(ethylene oxide) (75.00 mg), Methocel K 4M (6.30 mg), Aerosil 200 (3.60 mg), and magnesium stearate (4.00 mg). This mixture is then compressed to form tablets of about 9.25 mm in diameter weighing approximately 315 mg.

The compressed nuclei are then coated with a solution containing cellulose acetate (19.45 mg), cellulose acetate butyrate (13.90 mg) and poly (ethylene glycol) 400 (1.75 mg). The coating is carried out by applying a solution of the coating to the nuclei in a pulverizer while stirring. After coating, the coated cores are placed in a heated oven at 40° C. for a period of 12 hours. This first coating on each nucleus weighs approximately 35.0 mg upon completion of the coating.

A second coating is applied using about the same procedure used to prepare the first coating except that the components include Methocel E-15 (6.30 mg), Kollidon VA64 (4.52 mg), poly (ethyelene glycol) 6000 (1.80 mg), titanium dioxide (2.14 mg) and ferric oxide, red (0.24 mg). The second coating weighs approximately 15.00 mg upon completion.

The coating of the coated nuclei is then perforated using a laser. The laser beam is fired at a predetermined section of the coating with approximately 15–20 cm between the tablet and the beam orifice. The orifice is about 0.1 to 2 mm in diameter. The laser beam has a predetermined pulse period of 40 milliseconds.

The total weight of the finished tablet is about 365.10 mg.

EXAMPLE 2

A procedure for preparing 60 mg tablets is identical to that of Example 1 for preparing 30 mg tablets except that the weight of each ingredient is doubled, the second coating comprises cellulose acetate (31.42 mg), cellulose acetate butyrate (22.45 mg) and polyethylene glycol 400 (2.83 mg), the size of the core of the 60 mg tablet is approximately 10.5 mm in diameter, and the total weight of the tablet is about 706.70 mg.

EXAMPLE 3

The following process was used to prepare about 10,000 tablets of 30 mg strength Nifedipine-SOL.

In a laboratory mixer/kneader, micronized nifedipine (330.0 g), NaCl which had been sieved through a number 40 sieve (1,117.0 g), microcrystalline cellulose (363.0 g), povidone (500 g), PEO (50.0 g), hydroxypropyl methylcellulose (750.0 g), and colloidal silicon dioxide (21 g) are mixed to form a mixture. The mixture is then moistened with a solution containing polysorbate 20 (14.0 g) and ethyl alcohol 96% by wt. (400 ml). The moist mixture is sieved through a number 10 sieve and dried in an air-circulated oven at 45° C. for six hours. The dried granulate is sieved through a number 20 sieve. A granulate just prepared (3145 g) is placed in a double cone laboratory mixture and to it is added a mixture of colloidal silicon dioxide (15.0 g) and magnesium stearate, (40.0 g) which have been previously sieved through a number 50 sieve, and the mixture is mixed for ten minutes. This mixture is then compressed to form tables of 9.25 mm in diameter weighing approximately 320 mg and having a hardness of about 5 Kp.

The compressed nuclei are then coated with a solution containing cellulose acetate (333.4 g) and PEG 400 (17.6 g), which have been dissolved in a mixture of methylene chloride (6184 ml) and methanol (2566.0 ml). The coating is carried out in a conventional manner by applying a solution of the coating to the nuclei in a pulverizer being stirred without air. After coating, the coated cores are placed in a heated oven at 40° C. for a period of 12 hours. The coating on each nucleus will weigh approximately 35.1 mg upon completion of the coating.

The coating of the coated nuclei is then perforated using a laser. The laser beam is fired at a predetermined section of the coating to form an orifice, i.e, a preformed passageway, of about 0.1–2 mm in diameter. The laser beam has a predetermined pulse period of 40 milliseconds.

The coated and perforated nuclei are subsequently coated with a suspension containing HPMC (63.0 g), PEG 6000 (18.0 g), $TiO_2$ (21.4 g), iron oxide (2.4 g) and a mixture of methylene chloride (2324.0 ml) and ethyl alcohol 96% by wt. (996.0 ml). The weight of this second coating is approximately 15 mg per tablet and is applied to the cores in the same fashion as was done for the first coating. After the second coating, the coated cores are placed in a heated oven at 40° C. for a period of 12 hours.

EXAMPLE 4

A procedure for preparing 60 mg tablets is identical to that of Example 3 for preparing 30 mg tablets except that the weight of each ingredient is doubled, and the size of the core of the 60 mg tablet is approximately 10.5 mm in diameter.

EXAMPLE 5

A procedure for preparing once daily controlled release tablets containing carbamazepine (100 mg) follows. Carbamazepine (90.00 g), HPMC 2208 (4.00 g), NaCl (22.00 g), MCC (24.00 g), Povidone (23.00 g), and PEO (33.00 g; molecular weight of about 600,000) were mixed to form a mixture. The mixture is wetted with a blend of alcohol (96°, 70.0 ml) and polysorbate 20 (0.60 g) to form a blend. The blend was granulated and dried at 40–50° C. for 3 hours. It was then screened and mixed with 1.60 g of colloidal silicon dioxide. The granulate then mixed to homogeneity and to it was added magnesium stearate (1.80 g). The final blend was tabletted using biconcave 7.00 mm diameter punches to a hardness of 7–10 kP. The cores weighed 200.0 mg and contained approximately 100 mg of carbamazepine.

The cores were then coated with a composition containing: cellulose acetate (19.00 g) and PEG 400 (1.00 g) in a mixture of methylene chloride (350 ml) and methanol (140 ml). The composition was sprayed onto the cores in a conventional pan coater to obtain film coated tablets with a semipermeable membrane weighing about 20.0 mg. A hole (0.75 mm) was drilled through the coating in one face of the tablet.

An external coat was applied to the semipermeable membrane as follows. A composition containing HPMC 2910 (13.65 g), PEG 6000 (2.59 g) and TiO2 (3.31 g) in a mixture of methylene chloride: ethyl alcohol 96° (70:30, v/v) was prepared. This composition was sprayed onto the semipermeable membrane-coated tablets in a conventional pan coater until the external coat weight approximately 15 mg.

EXAMPLE 6

A procedure for preparing once daily controlled release tablets containing nimodipine (30 mg) follows. Carbamazepine (30.00 g), HPMC 2208 (6.30 g), NaCl (117.00 g), MCC (30.00 g), Povidone (50.00 g), and PEO (75.00 g; molecular weight of about 600,000) were mixed to form a mixture. The mixture is wetted with a blend of alcohol (96°, 120.0 ml) and polysorbate 20 (1.40 g) to form a blend. The blend was granulated and dried at 40–50° C. for 3 hours. It was then screened and mixed with 3.60 g of colloidal silicon dioxide. The granulate then mixed to homogeneity and to it was added magnesium stearate (4.00 g). The final blend was tabletted using biconcave 9.00 mm diameter punches to a hardness of 7–10 kP. The cores weighed 312.0 mg and contained approximately 30 mg of nimodipine.

The cores were then coated with a composition containing: cellulose acetate (34.20 g) and PEG 400 (1.80 g) in a mixture of methylene chloride (700 ml) and methanol (290 ml). The composition was sprayed onto the cores in a conventional pan coater to obtain film coated tablets with a semipermeable membrane weighing about 36.0 mg. A hole (0.75 mm) was drilled through the coating in one face of the tablet.

An external coat was applied to the semipermeable membrane as follows. A composition containing HPMC 2910 (13.65 g), PEG 6000 (2.59 g) and TiO2 (3.31 g) in a mixture of methylene chloride: ethyl alcohol 96° (70:30, v/v) was prepared. This composition was sprayed onto the semipermeable membrane-coated tablets in a conventional pan coater until the external coat weight approximately 15 mg.

The above is a detailed description of particular embodiments of the invention. It will be appreciated that, although specific embodiments of the invention have been described herein for purposes of illustration, various modifications may be made without departing from the spirit and scope of the invention. Accordingly, the invention is not limited except as by the appended claims. All of the embodiments disclosed and claimed herein can be made and executed without undue experimentation in light of the present disclosure.

What is claimed is:

1. An osmotic device comprising a core comprising an active agent and at least one excipient, a semipermeable membrane surrounding the core and comprising a preformed passageway that increases in size during use and an optical scored region of the membrane adjacent the passageway, wherein the preformed passageway is larger after use than it is prior to use of the osmotic device, and the internal pressure of the device increases during use causing a membrane edge defining the passageway to rupture.

2. The osmotic device of claim 1, wherein the release rate of active agent increases during use.

3. The osmotic device of claim 1, wherein the amount of active agent released is greater than that amount of active agent released by another osmotic device of approximately similar construction but not having a preformed passageway that increases in size.

4. The osmotic device of claim 1, wherein at least 80% of the active agent is released by the end of use.

5. The osmotic device of claim 1, wherein at least 90% of the active agent is released by the end of use.

6. The osmotic device of claim 1, wherein the preformed passageway increases in size by at least 10%.

7. The osmotic device of claim 1, wherein the preformed passageway increases in size by at least 25%.

8. The osmotic device of claim 1, wherein the preformed passageway increases in size by at least 50%.

9. The osmotic device of claim 1, wherein the preformed passageway increases in size by at least 75%.

10. The osmotic device of claim 1, wherein the preformed passageway increases in size by at least 100%.

11. The osmotic device of claim 1, wherein the preformed passageway is formed by mechanical means during manufacture of the osmotic device.

12. The osmotic device of claim 1, wherein the preformed passageway is plugged with a soluble material that dissolves during use of the osmotic device.

13. The osmotic device of claim 1, wherein the preformed passageway increases in size by dissolution or breakage of the semipermeable membrane.

14. The osmotic device of claim 1, wherein the semipermeable membrane dissolves or tears in a predetermined manner.

15. The osmotic device of claim 1, wherein the shape of the preformed passageway after enlargement approximates a predetermined shape.

16. The osmotic device of claim 1, wherein the core comprises a first layer comprising the active agent and the at least one excipient and a second layer comprising a swellable material or an osmotic agent.

17. The osmotic device of claim 1, wherein the core comprises a nucleus comprising a swellable material or an osmotic agent and a coating surrounding the nucleus and comprising the active substance and the at least one excipient.

18. The osmotic device of claim 1 further comprising one or more coatings on the exterior of the semipermeable membrane.

19. The osmotic device of claim 18, wherein the one or more coatings are independently selected at each occurrence from the group consisting of:
a drug-containing coating, a release rate modifying coating, a porous coating; a soluble coating, an insoluble coating, a semipermeable membrane; and a delayed release coating.

20. The osmotic device of claim 1, wherein the extent to which the passageway increases in size is related to the viscosity, molecular weight or degree of substitution of the at least one excipient.

21. The osmotic device of claim 1, wherein an increase in the viscosity, molecular weight or degree of substitution of the at least one excipient is related to an increase in the extent to which the passageway increases in size.

22. The osmotic device of claim 1, wherein the at least one excipient is independently selected at each occurrence from the group consisting of an osmagent, an osmopolymer, a lubricant, a glidant, adsorbent, antioxidant, buffering agent, colorant, flavorant, sweetening agent, tablet antiadherent, tablet binder, tablet and capsule diluent, tablet direct compression excipient, tablet disintegrant, tablet opaquant and tablet polishing agent.

23. An osmotic device comprising:
a core comprising an osmopolymer and an active agent;
a semipermeable membrane surrounding the core;
a preformed passageway in the semipermeable membrane; and
an optional scored region in the membrane adjacent the passageway;
wherein the passageway increases in size during use, the preformed passageway is larger after use than it is prior to use of the osmotic device, the internal pressure of the device increases during use causing a membrane edge defining the passageway to rupture, and the release rate of the active agent increases during use or the amount of active agent released is greater than that amount of active agent released from another osmotic device of approximately similar construction but not having a passageway that increases in size during use.

24. The osmotic device of claim 23, wherein the preformed passageway increases in size in a predetermined manner.

25. The osmotic device of claim 23, wherein the preformed passageway increases in size in a manner in a random manner.

26. The osmotic device of claim 23, wherein the semipermeable membrane dissolves or breaks to effect an increase in the size of or a change in the shape of the preformed passageway.

27. The osmotic device of claim 23, wherein the semipermeable membrane is adapted to dissolve or break in a predetermined manner.

28. The osmotic device of claim 23, wherein the release rate of active agent increases during use.

29. The osmotic device of claim 23, wherein the amount of active agent released is greater than that amount of active agent released by another osmotic device of approximately similar construction but not having a preformed passageway that increases in size.

30. The osmotic device of claim 23, wherein at least 80% of the active agent is released by the end of use.

31. The osmotic device of claim 23, wherein at least 90% of the active agent is released by the end of use.

32. The osmotic device of claim 23, wherein the preformed passageway increases in size by at least 10%.

33. The osmotic device of claim 23, wherein the preformed passageway increases in size by at least 25%.

34. The osmotic device of claim 23, wherein the preformed passageway increases in size by at least 50%.

35. The osmotic device of claim 23, wherein the preformed passageway increases in size by at least 75%.

36. The osmotic device of claim 23, wherein the preformed passageway increases in size by at least 100%.

37. The osmotic device of claim 23, wherein the preformed passageway is formed by mechanical means during manufacture of the osmotic device.

38. The osmotic device of claim 23, wherein the preformed passageway is plugged with a soluble material that dissolves during use of the osmotic device.

39. The osmotic device of claim 23, wherein the preformed passageway increases in size by dissolution or breakage of the semipermeable membrane.

40. The osmotic device of claim 23, wherein the semipermeable membrane dissolves or tears in a predetermined manner.

41. The osmotic device of claim 23, wherein the shape of the preformed passageway after enlargement approximates a predetermined shape.

42. The osmotic device of claim 23, wherein the core comprises a first layer comprising the active agent and the at least one excipient and a second layer comprising a swellable material or an osmotic agent.

43. The osmotic device of claim 23, wherein the core comprises a nucleus comprising a swellable material or an osmotic agent and a coating surrounding the nucleus and comprising the active substance and the at least one excipient.

44. The osmotic device of claim 23, further comprising one or more coatings on the exterior of the semipermeable membrane.

45. The osmotic device of claim 44, wherein the one or more coatings are independently selected at each occurrence from the group consisting of:
   a drug-containing coating, a release rate modifying coating, a porous coating; a soluble coating, an insoluble coating, a semipermeable membrane and a delayed release coating.

46. The osmotic device of claim 23, wherein the extent to which the passageway increases in size is related to the viscosity, molecular weight or degree of substitution of the at least one excipient.

47. The osmotic device of claim 23, wherein an increase in the viscosity, molecular weight or degree of substitution of the at least one excipient is related to an increase in the extent to which the passageway increases in size.

48. The osmotic device of claim 23, wherein the at least one excipient is independently selected at each occurrence from the group consisting of an osmagent, an osmopolymer, a lubricant, a glidant, adsorbent, antioxidant, buffering agent, colorant, flavorant, sweetening agent, tablet antiadherent, tablet binder, tablet diluent, tablet direct compression excipient, tablet disintegrant, tablet opaquant, and tablet polishing agent.

49. A method for making an osmotic device having a preformed passageway that increases in size during use comprising the steps of:
   forming a core comprising an active agent and at least one excipient;
   covering said core with a semipermeable membrane; and
   perforating said semipermeable membrane with a laser to form at least one preformed passageway that increases in size during use of the osmotic device and optionally to form at least one scored region in the membrane adjacent the passageway,
   whereby the internal pressure of the device increases during use causing a membrane edge defining the passageway to rupture.

50. The method of claim 49, wherein the perforating step comprises the step of:
   perforating said semipermeable membrane by firing a laser beam at a predetermined section of said semipermeable membrane for a predetermined period of time, the laser having a predetermined pulse period and a predetermined pulse width sufficient to form a preformed passageway that increases in size during use.

51. The method of claim 49, wherein the formation of said preformed passageway comprises unplugging the preformed passageway by dissolution of a soluble material during use of the osmotic device.

52. The method of claim 49, wherein said increase in size of said passageway is caused by tearing said semipermeable membrane.

53. The method of claim 49 further comprising the step of:
   covering the semipermeable membrane and plugging the preformed passageway with another coating.

54. The method of claim 53 wherein the other coating is a water soluble coating.

55. The method of claim 49 further comprising the steps of:
   covering the semipermeable membrane and plugging the preformed passageway with an inert first water soluble coating; and
   covering the first water soluble coating with an active agent-containing second water soluble coating.

56. The method of claim 55, wherein the step of perforating comprises:
   perforating the semipermeable membrane with a laser such that a preformed passageway having at least one adjacent etching is formed.

57. The osmotic device of claim 23 comprising:
   a core comprising an osmopolymer, an osmagent, an active agent, at least one other pharmaceutical excipient;
   a semipermeable membrane surrounding the core and comprising at least one cellulose ester and a plasticizer; and
   a preformed passageway in the semipermeable membrane;
   wherein the passageway increases in size during use and the release rate of the active agent increases during use or the amount of active agent released is greater than that amount of active agent released from a similar osmotic device not having a passageway that increases in size during use.

58. The osmotic device of claim 57 further comprising:
   an inert water soluble coating surrounding the semipermeable membrane and plugging the preformed passageway.

59. The osmotic device of claim 58 further comprising:
   an external active agent-containing coating surrounding the inert water soluble coating.

60. The osmotic device of claim 59, wherein the active agent is nifedipine, the osmopolymer is hydroxypropyl methylcellulose, the osmagent is sodium chloride, the at least one cellulose ester is cellulose acetate, and the plasticizer is poly(ethylene oxide).

61. The osmotic device of claim 57, wherein the semipermeable membrane comprises at least one etched portion adjacent the preformed passageway and the preformed passageway increases in size along the etched portion.

62. A controlled release device that provides a controlled release of an active agent during use, the device comprising:
   a core comprising an active agent and at least one excipient, wherein the core undergoes an increase in internal pressure during use of the device and after exposure of the core to an aqueous medium;
   a membrane surrounding the core and comprising at least one preformed passageway that increases in size during use of the device, and optionally comprising a scored region adjacent the at least one preformed passageway; wherein
   the increase in internal pressure of the device causes a membrane edge defining the passageway to rupture and the passageway to increase in size.

* * * * *

UNITED STATES PATENT AND TRADEMARK OFFICE
CERTIFICATE OF CORRECTION

PATENT NO. : 6,599,284 B2  
APPLICATION NO. : 09/728859  
DATED : July 29, 2003  
INVENTOR(S) : Joaquina Faour It is certified that error appears in the above-identified patent and that said Letters Patent is hereby corrected as shown below:

In Col. 26, line 53, replace the term "optical" with the term -- optional --.

Signed and Sealed this

Twenty-ninth Day of January, 2008

JON W. DUDAS  
*Director of the United States Patent and Trademark Office*